United States Patent
Luthra et al.

(10) Patent No.: US 7,771,743 B1
(45) Date of Patent: Aug. 10, 2010

(54) INFECTION RESISTANT POLYMERS, THEIR PREPARATION AND USES

(75) Inventors: Ajay Kumar Luthra, Middlesex (GB); Shivpal Singh Sandhu, Berkshire (GB)

(73) Assignee: BioInteractions, Ltd., Reading (GB)

( * ) Notice: Subject to any disclaimer, the term of this patent is extended or adjusted under 35 U.S.C. 154(b) by 0 days.

(21) Appl. No.: 09/980,697

(22) PCT Filed: Apr. 28, 2000

(86) PCT No.: PCT/GB00/01644

§ 371 (c)(1),
(2), (4) Date: Aug. 14, 2002

(87) PCT Pub. No.: WO00/65915

PCT Pub. Date: Nov. 9, 2000

(30) Foreign Application Priority Data

May 1, 1999 (GB) .................................. 9910042.2

(51) Int. Cl.
*A01N 25/00* (2006.01)
*A61K 9/00* (2006.01)
*C08F 26/00* (2006.01)

(52) U.S. Cl. ..................... 424/429; 424/406; 424/407; 424/411; 526/248

(58) Field of Classification Search .................. 424/484, 424/411, 406, 407, 422, 429; 514/772.4; 526/248
See application file for complete search history.

(56) References Cited

U.S. PATENT DOCUMENTS

| | | | |
|---|---|---|---|
| 2,084,466 A | 6/1937 | Ukropina | |
| 3,695,921 A | 10/1972 | Shepherd et al. | |
| 4,479,795 A | 10/1984 | Mustacich et al. | |
| 4,537,746 A * | 8/1985 | Ogunbiyi et al. | 422/28 |
| 4,581,028 A | 4/1986 | Fox, Jr. et al. | |
| 4,678,660 A | 7/1987 | McGary et al. | |
| 4,713,402 A | 12/1987 | Solomon | |
| 4,891,423 A | 1/1990 | Stockel | |
| 5,142,010 A * | 8/1992 | Olstein | 526/248 |
| 5,288,503 A | 2/1994 | Wood et al. | |
| 5,451,424 A * | 9/1995 | Solomon et al. | 427/2.1 |
| 5,707,366 A | 1/1998 | Solomon et al. | |
| 5,817,325 A * | 10/1998 | Sawan et al. | 424/411 |
| 5,886,048 A | 3/1999 | Kirschner et al. | |
| 5,928,916 A | 7/1999 | Keogh | |
| 6,929,818 B2 | 8/2005 | Luthra et al. | |

FOREIGN PATENT DOCUMENTS

| | | |
|---|---|---|
| EP | 0103776 A | 3/1984 |
| EP | 0379269 B1 | 7/1990 |
| EP | 0490250 | 6/1992 |
| EP | 0460385 A | 12/1999 |
| GB | 978855 | 12/1964 |
| GB | 1531717 | 11/1978 |
| GB | 1531717 A * | 11/1978 |
| GB | 2084466 A | 4/1982 |
| GB | 2085454 A | 4/1982 |
| GB | 2349644 A | 8/2000 |
| JP | 5717913 | 10/1982 |
| JP | 59161414 | 9/1984 |
| JP | 59228856 | 12/1984 |
| JP | 62230806 A | 10/1987 |
| JP | 3039310 | 2/1991 |
| JP | 5097697 | 4/1993 |
| JP | 6036064 | 2/1994 |
| JP | 408073595 A * | 3/1996 |
| JP | 08 226077 | 9/1996 |
| RO | 112577 | 11/1997 |
| RO | 113302 | 6/1998 |
| WO | WO 86/02561 | 5/1986 |
| WO | 9504520 A1 | 2/1995 |
| WO | WO 98/2073 A1 * | 5/1998 |

OTHER PUBLICATIONS

Ikeda et al, New Polymeric Biocides: Sythesis and Antibacterial Activity of Polycationis with Pendant Biguanide Groups; Aug. 1984, Antimicrobial Agents and Chemotherapy, vol. 26, No. 2, p. 139-144.*
Gottsauner-Wolf Et Al. In Clin. Cardiol. 19, 347-356 (1996) "Restenosis—an open file".
Mariotti, et al., "Chlorhexidine-induced changes to human gingival fibroblast collagen and non-collagen protein production" Journal of Periodontology, vol. 70, No. 12, Dec. 1999.
Pitfield, et al., "Effect of chlorehexidine on gingival epithelial cell growth and migration", Journal of Dental Research, vol. 72 p. 336 (Abstract).
Shakespeare et al., "Effects of proprietary oral rinses containing chlorhexidine, hexetidine and benzydamine on the proliferation of human buccal epithelial cells in culture." Archives of Oral Biology England 1988, vol. 33, No. 12.
Xu, "In Vitro Prompt killing by chlorhexidine of human colorectal crcinoma cell lines." Chinese Journal of Surgery (1990) vol. 28, No. 1.
Great Britain, British Patent Office Search Report, Jul. 8, 1999.
JP Patent Abstract vol. 12 No. 103 (C-485), Apr. 5, 1988.
JP Patent Abstract col. 1997 No. 1, Jan. 31, 1997.
Patent Cooperation Treaty, International Search Report, Nov. 9, 2000.

* cited by examiner

*Primary Examiner*—Michael G Hartley
*Assistant Examiner*—Micah-Paul Young
(74) *Attorney, Agent, or Firm*—Dardi & Herbert, PLLC

(57) ABSTRACT

A family of infection resistant and biocidal polymeric materials incorporates an infection resistant biguanide such as chlorhexidine or polyhexanide pendant to the polymer chain, chemically linked to the polymer through the biguanide group secondary nitrogen atoms. The disclosure extends to the use of such polymeric materials in articles of manufacture and particularly in medical devices, and the preparation of the materials as polymer resins from which articles can be made, as solutions and emulsions which can be used for coating performed articles, and in situ on the surface of preformed polymeric articles.

7 Claims, No Drawings

INFECTION RESISTANT POLYMERS, THEIR PREPARATION AND USES

FIELD OF THE INVENTION

This invention relates to infection resistant polymers, methods for their preparation, and their uses. In particular the invention concerns a family of polymeric materials incorporating an infection resistant biguanide compound pendant to the polymer chain, the use of such polymeric materials in articles of manufacture and particularly in medical devices, and the preparation of the materials as polymer resins from which articles can be made, as solutions and emulsions which can be used for coating preformed articles, and in situ on the surface of preformed polymeric articles.

BACKGROUND OF THE INVENTION

Medical apparatus, for example, medical devices such as contact lenses, catheters for vascular access (both arterial and venous), abdominal cavity tubing, drainage bags and connectors of various kinds, are required to be infection resistant. The desirable feature of such medical apparatus is control of infection that occurs during the application of the 20, apparatus when in contact with body tissue or fluid. The term medical device as used herein is intended to encompass the full range of devices for intimate contact with the human or other mammalian body, or with the corresponding body fluids, as implants, prostheses, interface devices, surgical equipment and the like.

Fabrication of medical apparatus is usually from polymeric materials that may comprise, but are not limited to, polyurethanes, silicones, polyvinylchloride and others, by moulding and extrusion techniques.

There are many cited efforts to eradicate the problem of infection on medical apparatus. These have largely been aimed at attaching the infection resistant material to the polymeric apparatus.

U.S. Pat. No. 3,695,921 discloses a layer of hydrophilic polymer on a catheter that is able to absorb an antibiotic. Thermoplastic polyurethane medical devices containing an anti-microbial agent on their surface are described.

U.S. Pat. No. 4,581,028 discloses infection resistant vascular grafts with incorporated anti-microbial agents, such as silver sulphadiazine and pipericillin.

U.S. Pat. No. 4,479,795 describes medical apparatus of permeable polymers, which incorporate releasable anti-microbial agent that is able to diffuse to the surface to form a barrier.

As disclosed in a Japanese Patent Application No. 60/36064 chlorhexidine is adsorbed on to the surface of polyurethane or silicone catheter by dipping into an aqueous solution of chlorhexidine and then converted to a water insoluble form by dipping into a solution of an acid.

Japanese Patent Application No 59/228,856 discloses an elastomeric catheter possessing a water insoluble biguanide or salt as a thin coating on the surface.

PCT Application No WO 86/02561 discloses a thermoplastic polymer having up to 1% chlorhexidine contained in or upon the surface.

UK Patent Application No 2,084,466A discloses a procedure for rendering polypropylene apparatus biocidal with chlorhexidine base, and suggests that the apparatus may be prepared from other plastics.

Solomon at el., in U.S. Pat. No. 4,713,402, discloses the bonding of a quaternary salt to the surface of a polymeric apparatus and the attachment of an antibiotic to the salt.

In U.S. Pat. No. 4,678,660 there is disclosure of a polyurethane article having on the surface a layer of a polyurethane alloy consisting of a dispersed complex of a quaternary salt with an antibiotic.

Solomon et al. describe in U.S. Pat. No. 5,451,424 a method for preparing medical apparatus by a homogenous melt of polymer and chlorhexidine and having bulk distributed chlorhexidine U.S. Pat. No. 4,891,423 discloses linear polyoxyalkylene diamine biguanides and discusses other known biguanides, and their use in solid and liquid bactericidal and fungicidal compositions, including ophthalmic saline solutions.

U.S. Pat. No. 5,142,010 discloses the vinyl copolymerisation of certain polymerisable unsymmetrical biguanide compounds.

U.S. Pat. No. 5,817,325 discloses crosslinking biguanide polymers with, inter alia, isocyanates or epoxides to form an immobile, insoluble, non-leachable surface matrix which has the ability to deliver deposited biocidal silver salts into a the interior of a micro-organism. The polymers are useful for coating contact lens cases and other articles. The biocidal action is through the silver salts, not through the highly cross-linked biguanides.

Even though the methods for preparing infection resistant medical apparatus have addressed some of the problems, they are, however, not adequately effective. A major constraint is that the infection resistant material, when incorporated on to or into the apparatus, loses potency in inhibiting or reducing bacterial growth.

Another contributing factor is that the bulk distribution of the infection resistant material is not stable and in certain cases is able to permeate from the apparatus into body tissue or fluid and cause harmful effects.

SUMMARY OF THE INVENTION

In accordance with the invention, novel chemically modified infection resistant materials are produced by the chemical modification of infection resistant biguanide compounds to produce polymers that can be blended into the bulk of other polymers, be used as coatings, or be chemically attached to the surface of a medical device.

A medical device in accordance with the invention may be made of, coated with, or surface treated to form in situ, the novel polymers having infection resistant properties.

In this specification, references to infection resistant materials (IRMs) include antibiotics, anti-bacterial agents, anti-viral agents, anti-microbial agents, and the like. Infection resistant is taken to means capable of killing, preventing the proliferation of, or inhibiting or at least substantially slowing the growth of, susceptible classes of microorganisms. Microorganisms include but are not necessarily limited to bacteria, viruses, fungi, yeasts, algae and other life forms. IRMs include, but are not limited to, antibiotics, anti-bacterial agents, anti-viral agents and anti-microbial agents.

Biguanides are strongly basic compounds containing the biguanide group —NH—C(NH)—NH—C(NH)—NH— and have been identified as having powerful antimicrobial activity. Two particularly preferred biguanides for the purposes of the present invention are polyhexanide and chlorhexidine, which are commercially available. Each includes the biguanide group adjacent a hexamethylene chain. Their respective structures can be represented as follows:

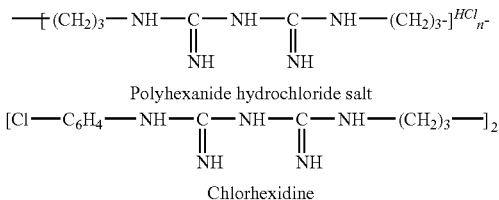

Polyhexanide hydrochloride salt

[Cl—C$_6$H$_4$—NH—C(=NH)—NH—C(=NH)—NH—(CH$_2$)$_3$—]$_2$

Chlorhexidine

Polyhexanide and chlorhexidine have a broad spectrum of anti-bacterial activity and at relatively low concentrations the anti-bacterial action is bacteriostatic; at higher concentration the action becomes rapidly bactericidal. The commercial water soluble salt of chlorhexidine is usually the digluconate.

In one aspect of the invention, infection resistant biguanides are chemically modified to yield novel chemically modified infection resistant materials.

In another aspect of the present invention the chemically modified infection resistant material is applied to medical devices to render them resistant to biological growth that induces infection.

In accordance with a further aspect of this invention, the application of the chemically modified infection resistant material to a medical device produces stable, non-leaching infection resistant material.

Without wishing to be bound by any particular theory, it is believed that the antimicrobial activity of biguanide compounds derives from the strongly basic character of their biguanide groups which form acid addition salts with a cationic charge delocalised over the five neighbouring secondary amine nitrogen atoms. This enables the biguanide to be rapidly attracted to a negatively charged bacterial cell. Thereafter the biguanide interacts with the cytoplasmic membrane, upsetting the ionic balances and, ultimately, disrupting the membrane and causing irreversible damage to the cell contents.

The present invention utilises the amino nitrogen atoms of the biguanide group to anchor these antimicrobial compounds to a polymeric substrate as pendant species without disabling their antimicrobial properties, although the normal acid addition salt form of these compounds interferes with their derivatisation at these amino sites. The polymeric products of the invention are thus distinguished from both linear polymeric biguanides and highly cross-linked biguanide polymers.

In accordance with the invention, there is provided a polymeric material incorporating an infection resistant biguanide compound pendant to the polymer chain, being chemically bound thereto through some but not all of the amine nitrogen atoms, and preferably of the secondary amine nitrogen atoms of the —NH—C(NH)—NH—C(NH)—NH— biguanide group or groups, of the infection resistant biguanide compound. The pendant biguanide compounds are generally bound through the secondary amine nitrogen atoms, which may include some of the >C=NH imino nitrogen atoms, and may include some of the C—NH—C secondary amine nitrogen atoms. However, a certain amount of binding through the primary amine groups at each end of biguanides such as polyhexanide is also possible.

There is also provided a medical device comprising a polymeric material incorporating a a pendant infection resistant biguanide compound chemically bound to the polymer through some but not all of the amine nitrogen atoms of the biguanide, and particularly the secondary amine nitrogen atoms of the —NH—C(NH)—NH—C(NH)—NH— biguanide group or groups of the infection resistant biguanide compound. Such a medical device may be formed from or coated with the polymeric material incorporating the infection resistant biguanide compound, or the medical device may first be formed from or coated with polymeric material which is thereafter chemically bound to some but not all of the nitrogen atoms of the infection resistant biguanide compound, or the medical device may first be formed from or coated with polymeric material which is thereafter chemically bound to the residuum of a non-polymeric compound that has been bound to some but not all of the nitrogen atoms of the infection resistant biguanide compound.

In other words, the biguanide can be incorporated as a pendant group into a polymer which is then made into or coated on to an article, or the biguanide can be chemically linked to polymer already on an article, or the biguanide can be bound to polymer on an article through an intermediate non-polymeric compound. Such a compound requires one functionality to bind with the biguanide secondary amine, and one functionality to bind with the polymer.

Polymer functionality to bind with the IRM directly (either to the biguanide secondary amine or to a functional group on a bound non-polymeric compound as described above) may include groups such as hydroxyl (—OH), carboxyl (—COOH), anhydride (—CO—O—CO—), isocyanate (—NCO), allyl, vinyl, acrylate, methacrylate, epoxide, sulfonic (—SO$_3^-$) or sulfate (—SO$_4^-$) groups. Linkage to the polymer may be by covalent bonding (including grafting) or by ionic bonding.

Chemical binding to a secondary amine nitrogen atom by means of isocyanate results in a substituted urea linkage, or by means of isothiocyanate results in a substituted thiourea linkage, or by means of expoxide results in a beta-hydroxyl-tertiary amine, or by means of acid chloride results in a N,N-disubstituted amide, or by means of acid anhydride results in a N,N-disubstituted amide, or by means of aldehyde or ketone results in N,N-disubstituted hemiaminals or aminals depending on the aldehyde or ketone, or by means of unsaturated bonds results in a tertiary amine linkage.

Suitable medical devices to which the invention may be applied include catheters, blood bags, dialysis or other membranes, surgical gloves, surgical instruments, vascular grafts, stents, contact lenses and intra-ocular lenses, contact lens cases, bottles, diagnostic apparatus, oxygenators, heart valves and pumps. A preferred medical device is formed as a contact lens or intra-ocular lens.

Other articles of manufacture to which the invention may be applied include kitchen equipment such as worktops and chopping boards. Polymeric IRMs may be applied to articles by sprays, to form thin surface films.

In a further aspect, the invention provides a method of making an infection resistant polymeric material which comprises chemically binding reactive sites on a polymeric material with some but not all of the amine nitrogen atoms of an infection resistant biguanide compound, especially the secondary amine nitrogen atoms of the —NH—C(NH)—NH—C(NH)—NH— biguanide group or groups of an infection resistant biguanide compound. The secondary amine nitrogen atoms bound to the reactive sites may include some of the >C=NH imino nitrogen atoms and may include some of the C—NH—C nitrogen atoms. Primary amine end groups on suitable biguanide compounds, such as polyhexanide, may also participate in binding to polymeric materials.

In an important aspect of the method, it comprises the preliminary step of forming a free base, preferably a partial free base, of the biguanide compound before binding the reactive sites with the nitrogen atoms. By removing some but not all of the acid of the usual acid addition salt, some of the secondary amine nitrogen atoms become available for derivatisation. If the entire free base is liberated, care needs to be taken to ensure only partial derivatisation.

The preferred reactive sites to bind with the biguanide nitrogen comprise isocyanate, isothiocyanate, epoxide, acid chloride, acid anhydride, aldehyde, ketone and unsaturated (especially acrylate, methacrylate and vinyl) sites.

Similar considerations apply to a variation of the above method which comprises modifying a polymer precursor by chemically binding some but not all of the amine nitrogen atoms of an infection resistant biguanide compound, especially the secondary amine nitrogen atoms of the —NH—C(NH)—NH—C(NH)—NH— biguanide group or groups of an infection resistant biguanide compound with reactive sites on the polymer precursor, and thereafter converting the so modified polymer precursor to an infection resistant polymeric material by a method including a polymerisation step which leaves the biguanide compound residue pendant to the polymer chain.

The reactive sites on the polymer precursor may comprise isocyanate, isothiocyanate, epoxide, acid chloride, acid anhydride, aldehyde, ketone or unsaturated sites, or other suitable sites. Even sites comprising hydroxyl, carboxyl or amino groups can link on to the biguanide groups by using coupling agents such as carbonyl diimidazole or carbidomides.

The polymer precursor may also contain acrylate, methacrylate, allyl or vinyl groups, and the polymerisation step may be carried out by polymerising the modified polymer precursor through the said groups. Any other polymerisable group may also be used.

Similar considerations apply to a further variation of the foregoing method of making an infection resistant polymeric material which comprises modifying a non-polymeric compound by chemically binding some but not all of the amine nitrogen atoms of an infection resistant biguanide compound, especially the secondary amine nitrogen atoms of the —NH—C(NH)—NH—C(NH)—NH— biguanide group or groups of an infection resistant biguanide compound with reactive sites on the non-polymeric compound, and thereafter chemically binding the so modified compound to a polymeric material. The chemical binding of the IRM to the polymeric material may be by covalent bonding (including grafting) or by ionic bonding.

The non-polymeric compound may also contain acrylate, methacrylate, allyl or vinyl groups, so that the modified compound may be chemically bound to a polymeric material through the said groups. Any other polymerisable group may also be used. Other functional groups carried by the non-polymeric compounds for binding with polymeric materials may include hydroxyl, carboxyl, amide, amino, epoxide, isocyanate, sulfate, sulfonate and others. In general, it is possible to provide functionality that can react with available complementary chemical constituents contained in polymeric materials to form polymeric infection resistant materials or to covalently attach to surfaces.

Whichever method of preparation is used, the resulting polymer containing biguanide groups may be subsequently blended with other polymeric material to form an infection resistant polymer blend for use in forming an article of manufacture, and preferably blended with medically acceptable polymeric material to form an infection resistant medical polymer blend for use in the manufacture of a medical device.

Typical materials for blending include polyurethanes, polyamides, latex, silicones, siloxanes, polyvinyl chloride, polyesters, polycarbonates, polyacrylonitrile, polymethylmethacrylate, polypropylene, polyethylene and hydrogels. Clearly the biguanide polymer and the blending polymer should be suitably compatible.

The resulting polymer containing biguanide groups may be subsequently blended with ocularly acceptable lens material to form an infection resistant ocular polymer blend for use in the manufacture of a contact or intra-ocular lens.

Alternatively, the resulting polymer containing biguanide groups may include acrylate, methacrylate, allyl or vinyl groups, and the polymer may be subsequently copolymerised with ocularly acceptable lens material to form an infection resistant ocular polymer for use in the manufacture of a contact or intra-ocular lens.

Typical lens materials include, but are not limited to, hydroxyethyl methacrylate, methyl methacrylate, vinyl pyrrolidone, silicone or siloxane methacrylates, fluorocarbon methacrylates, polyvinyl pyrrolidone, polyvinyl alcohol, polyethylene oxide, and polyethylene glycol. These polymers may contain zwitterionic functionality. Lenses can be ionic or non-ionic.

Suitable zwitterionic monomers for polymerisation include 2-(methacryloyloxyethyl)-2'-(trimethylammonium) ethyl phosphate inner salt and any containing phosphorylcholine groups.

In a further application of the invention, the polymer containing biguanide groups may subsequently be coated on to an article of manufacture to form an infection resistant coating thereon.

Chlorhexidine and polyhexanide are the preferred biguanide compounds. Each has its own activity spectrum. To broaden the antimicrobial range of the end product, the invention includes the further step of blending the resulting polymers containing biguanide groups derived from both chlorhexidine and polyhexanide, or copolymerising precursors to form a polymer in accordance with the invention containing biguanide groups derived from both chlorhexidine and polyhexanide.

The IRM may exist in the free base or acid form or the salt thereof and as such the invention does include such forms.

DETAILED DESCRIPTION OF THE INVENTION

To illustrate the invention by a general example, an amino constituent contained in the derivatised biguanide infection resistant material (IRM-NH$_2$) is able to react with a polymeric isocyanate (P—NCO) constituent to form a urea linkage giving a polymeric infection resistant material, as outlined in Scheme 1 a), b) and c). The converse is also true where the IRM contains isocyanate constituents and is able to react with polymeric amino.

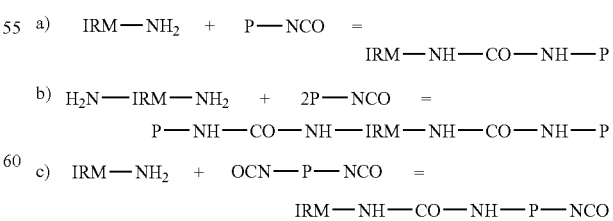

Polymeric Infection Resistant Materials (PIRM) prepared as in Scheme 1 may be constituted, by way of example, into homogeneous blends of extrudable polyurethane to form medical apparatus with anti-bacterial properties that are effective and stable, in which the PIRM is unable to permeate to body tissue or fluids.

By way of another example the PIRM is prepared and dissolved in a suitable solvent for coating the medical article in order to give it anti-bacterial properties that are effective and stable, in which the PIRM is unable to permeate to body tissue or fluids.

By way of a further example the chemically modified IRM (e.g. IRM-NH$_2$) is attached to the surface by conventional chemical linkages. In the case of IRM-NH$_2$, one such method would by way of an amide bond.

An example of chemical modification, in relation to polyhexanide, is the reaction of an isocyanate to the secondary amine, as shown by Scheme 2, to give substituted ureas.

Scheme 2.

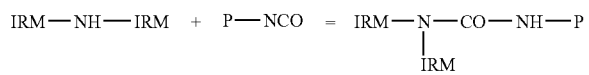

The polyisocyanates useful in the invention in producing substituted ureas with the IRM, typically polyhexanide, may be selected from a wide range of aliphatic, cycloaliphatic, and aromatic polyisocyanates. The isocyanate groups may be carried on polymers having unsaturated alkyl groups, esters, ethers, siloxanes, urethanes, amides, carbonates, and mixtures thereof which can be chosen to promote compatibility with other polymers that they may subsequently be coated on or blended with.

Polydiisocyanates that can be utilised are those typically used in the formation of polyurethane, which when reacted with secondary amines form the substituted ureas.

Additionally, polydiisocyanates can be prepared by the reaction of a polyamine or polyol with a diisocyanate, as shown by Scheme 3.

Scheme 3

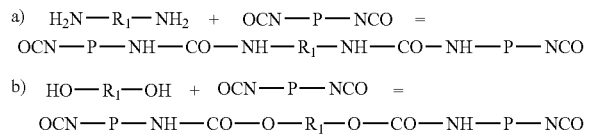

In Scheme 3, —R$_1$— and —P— can typically be aliphatic groups, cycloaliphatic groups, aromatic groups, unsaturated alkyl groups, esters, ethers, siloxanes, urethanes, amides, carbonates, and mixtures thereof. Others are of course possible.

Such polydiisocyanates may then be further reacted with IRM containing appropriate reactive chemical groups, an example being the secondary amine of polyhexanide reacted with the isocyanates, as shown in Scheme 4; thus producing Polymeric Infection Resistant Materials (PIRM).

Scheme 4

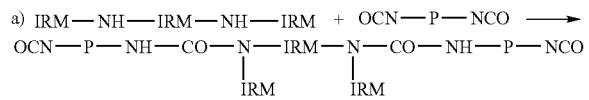

-continued

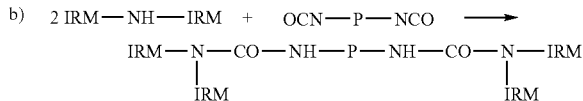

The PIRM can be compounded with other polymers, such as polyurethanes, polysiloxanes, polyesters, polyvinylchlorides, polybutadienes and polyamides, to produce medical apparatus, either by extrusion or moulding, that are infection resistant. The active ingredient (IRM) is stable within the medical apparatus and is non-leaching.

The PIRM or the IRM may contain allyl, vinyl, acrylate or methacrylate groups for polymerisation to form allyl, vinyl, acrylate, and methacrylate type polymers.

Allyl, vinyl, acrylate and methacrylate functionalities can be incorporated in the IRM by reacting the acid chloride, isocyanate, epoxide or anhydride of a molecule containing the above double bond functionality.

For instance, methacryloylchloride can be reacted with the secondary amine of a biguanide resulting in the formation of a tertiary amide with the liberation of hydrogen chloride which re-forms the hydrochloride on the biguanide group.

Isocyanatoethyl methacrylate, allyl isocyanate, glycidyl methacrylate and the anhydride or mixed anhydride of methacrylic acid can undergo reactions with the free base of the biguanide to yield methacrylate and allyl functionality on the biguanide group. The isocyanate would react to form a urethane urea bond, the epoxide would react to form a tertiary amine and the anhydride to form a tertiary amide.

Methacrolein can also react with the secondary amine of the biguanide. Here the reaction is between a secondary amine and an aldehyde which can yield a hemiaminal or aminal, depending on the aldehyde.

Allyl, vinyl, acrylate and methacrylate derivatives of IRMs can undergo homopolymerisation or copolymerisation with numerous other molecules or polymers which have a double bond under thermal or electromagnetic radiation. The allyl, vinyl, acrylate and methacrylate derivatives of IRMs can be grafted on to surfaces having functional groups, eg OH, COOH, SO$_3^-$, SO$_4^-$, NH$_2$, by using initiators such as cerric ammonium nitrate.

Conversely the free base of the biguanide can react with acrylate and methacrylate derivatives of monomers or polymers to produce PIRM.

The PIRM may be dissolved in a suitable solvent, such as alcohols, acetone or tetrahydrofuran (THF) or mixtures thereof and coated on to medical apparatus. Dipping, spraying, or any other means by which a homogenous coating may be obtained, following by any necessary drying out, can be used to place the coating of PIRM on to the medical apparatus. The articles to be coated may be made of plastics, metals, composites or any other material compatible with the intended coating.

The invention is illustrated by the following non-limiting examples. Examples 1 and 2 concern the preparation of polyhexanide partial free-base, which is necessary in order to protect some of the biologically active sites while freeing others to participate in reactions, in order to prepare active infection-resistant derivatives.

Polyhexanide is a commercial anti-microbial agent manufactured by Zeneca Biocides and can be represented by the following general formula:

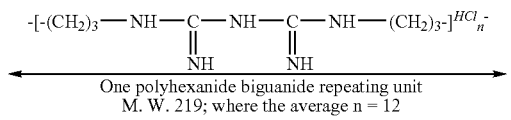

One polyhexanide biguanide repeating unit
M. W. 219; where the average n = 12

In order to derivatise polyhexanide, at least some of the hydrochloride groups must be removed. The hydrochlorides can be neutralised with a strong base, for example, sodium hydroxide.

Either all the hydrochloride groups associated with the biguanide groups of the polyhexanide can be neutralised and then the desired chemistry carried out before re-forming their hydrochloride salts or only the desired number of hydrochlorides can be neutralised and then the chemistry carried out before re-forming their hydrochlorides. Both are acceptable methods of derivatisation.

Similar considerations apply to chlorhexidine and other biguanide compounds.

Example 1

Polyhexanide Starting Material 400 ml of a 20% w/v aqueous solution of polyhexanide (Zeneca Biocides) was placed in a Spectra/Por® membrane (MWCO: 2,000) and was dialysed against 10 liters of deionised water for 16 hrs. The dialysed polyhexanide was then placed in stainless steel freeze-drying trays and was freeze dried for 72 hrs.

The yield of dry crystalline powder of polyhexanide was 40 g.

Example 2

Partial Free-Base Polyhexanide

In this example only 1 in 6 biguanide hydrochloride groups are neutralised.

1 g ($4.5662 \times 10^{-3}$ moles of biguanide hydrochloride groups) of polyhexanide powder (from Example 1) was dissolved in 80 ml deionised water. The number of moles of sodium hydroxide required to neutralise 1 in 6 biguanide hydrochloride groups of polyhexanide is $7.61 \times 10^{-4}$ moles (0.0304 g, NaOH). Sodium hydroxide (0.0304 g) was dissolved in 50 ml deionised water and added drop-wise to the polyhexanide solution over a period of 1 hr. The solution was then freeze-dried yielding a dry crystalline powder of polyhexanide partial free-base (Ph.P free-base).

Example 3

Polyhexanide/Polyisophorone Urethane Polymer 1.027 g ($7.61 \times 10^{-4}$ moles) Poly (neopentyl glycol adipate) isophorone diisocyanate terminated (PNGAID, Mn 1350) (Aldrich Chemical Co.) was dissolved in 50 ml dichloromethane. 1 g of Ph.P free-base (from Example 2) was dissolved in 50 ml ethanol and was vigorously stirred. To this polyhexanide was added the above PNGAID solution over a period of 1 hr, to form urethane urea bonds. The solution was neutralised with 0.019 ml of 4M hydrogen chloride in 1,4 dioxane.

Infrared spectrum showed the disappearance of the band at 2265.9 cm due to the N=C=O group.

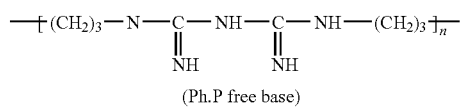

(Ph.P free base)

1) ONC-R-NCO
2) HCl in 1,4-dioxane (Where R represents the poly(neopentyl glycol adipate) isophorone moiety)

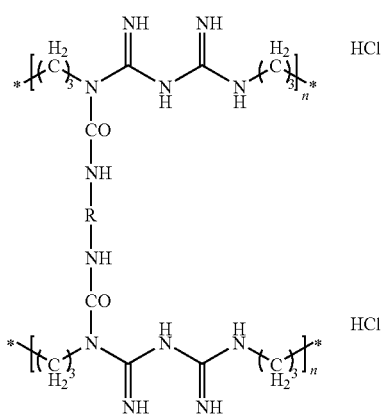

Example 4

Polyhexanide/Silicone Copolymer 4.158 g ($3.08 \times 10^{-3}$ moles) PNGAID was dissolved in 50 ml anhydrous dichloromethane and stirred vigorously. 41.58 g ($1.54 \times 10^{-3}$ moles) aminopropyl terminated polydimethylsiloxane (APDS) with an average molecular weight of 27,000 (Gelect, Inc) was dissolved in 200 ml anhydrous dichloromethane, and was added drop-wise to the dichloromethane solution of PNGAID over a period of 2 hrs. The reaction formed urethane urea bonds between the PNGAID and APDS with the resulting copolymer terminating in isocyanate groups.

The infrared spectrum of the copolymer showed the existence of the band at 2265 cm$^{-1}$ due to the N=C=O group.

To the above PNGAID-APDS copolymer was added allylamine (0.088 g, $1.54 \times 10^{-3}$ moles) dissolved in 50 ml anhydrous dichloromethane over a period of 1 hr. This resulted in the introduction of one allyl functionality to the PNGAID-APDS copolymer leaving one reactive isocyanate.

1 g of Ph.P free-base (from Example 2) was dissolved in a mixture containing 40 ml ethanol and 10 ml dichloromethane. This solution was vigorously stirred and the above copolymer PNGAID-APDS was added dropwise over a period of 2 hrs. Infrared showed the disappearance of the N=C=O band at 2265 cm$^{-1}$. The secondary amine of the Ph.P free-base reacted with the isocyanate of the PNGAID-APDS copolymer to form a urethane urea bond.

The resulting solution was neutralised with 0.019 ml of 4M hydrogen chloride in 1,4 dioxane.

Example 5

Extruded Silicone Sheets

The copolymer resulting from Example 4 was dried initially on a rotary evaporator and then dried under vacuum at 50° C. for 16 hrs. The yield was 47 g of polyhexanide/silicone copolymer.

The above polyhexanide/silicone copolymer (47 g) was mechanically mixed in with Silastic Q7-4736 Biomedical grade ETR (1 Kg) obtained from Dow Corning. After 1 hr of mechanical mixing, sheets were extruded and cured at 120° C. for 30 minutes.

The high consistency silicone sheets containing polyhexanide moieties had tear strengths, elongation and tensile strength equivalent to those containing no polyhexanide/silicone copolymer.

Example 6

Polyhexanide Methacrylate 2.25 g (0.01027 moles of biguanide hydrochloride groups) of polyhexanide powder (from Example 1) was dissolved in de-ionised water. The number of moles of sodium hydroxide required to neutralise 1 in 12 biguanide hydrochloride groups of polyhexanide is $8.5616 \times 10^{-4}$ moles (0.03425 g NaOH). Sodium hydroxide (0.03425 g) was dissolved in 50 ml of de-ionised water and added dropwise to the vigorously stirred solution of polyhexanide partial free-base (Ph.P free-base).

The above Ph.P free-base was dissolved in 60 ml anhydrous dimethyl sulphoxide and stirred. 0.0895 g ($8.5616 \times 10^{-4}$ moles) methacryloyl chloride was dissolved in 25 ml dimethyl sulphoxide solution containing the Ph.P free-base over a period of 1 hr.

The above reaction involves the formation of a tertiary amide when the methacryloyl chloride reacts with the free secondary amine of the polyhexanide and the HCl liberated re-forms the hydrochloride of biguanide groups. Accordingly, when n=12, there is an introduction of one methacrylate group per polyhexanide polymer chain.

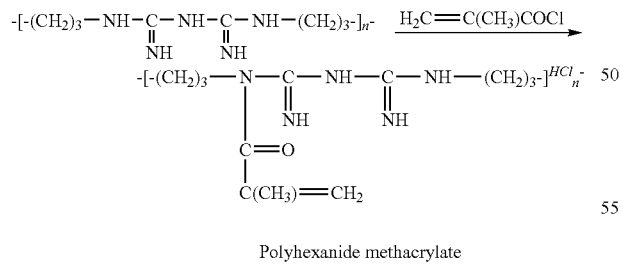

Polyhexanide methacrylate 500 ml of chloroform was then added to the above reaction mixture which precipitated the derivatised polyhexanide from solution. The solution was allowed to stand for 24 hrs at 3° C. and then washed with 3×100 ml of chloroform and then dried in a vacuum oven at 30° C. for 6 hrs.

The infrared spectrum showed the disappearance of the bands at 1765 and 1737 cm$^{-1}$ due to strong absorption of C=O unsaturated aliphatic acid chlorides.

The band due to tertiary amide

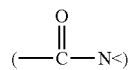

stretching in the region 1670-1630 is partially obscured by the absorption due to the polyhexanide.

Example 7

Contact Lens Formation 20 mg polyhexanide methacrylate (from Example 6) was dissolved in 10 ml 2-hydroxyethyl-methacrylate (Fluka) containing 40 mg ethylene glycol dimethacrylate and 20 mg 2,2'-azobis (2,4-dimethylvaleronitrile (Dupont)). The above clear solution was degassed for 30 min.

The above polymerisation mixture was poured into a polypropylene concave mould and then a polypropylene convex mould was placed onto the concave mould allowing the excess solution to overflow thereby uniformly filling the space between the concave and convex moulds. The shape of the concave and convex moulds approximates a contact lens. The sealed moulds were then heated to a temperature of 65° C. for 4 hrs and then at 110° C. for 1 hour.

The moulds were then cooled and opened and a contact lens was obtained. The lens produced was clear and transparent. The lens were hydrated in phosphate buffered saline for 6 hrs. The water content was 38% by weight.

Example 8

Polyhexanide Polymer Coated Tubing 20 g of polyhexanide methacrylate was synthesised according to Example 6.

A 2 liter, 3-necked reaction vessel equipped with stirrer, thermometer, condenser and nitrogen inlet tube was charged with 1000 ml of de-ionised water and placed in a silicone oil bath at 120° C. The solution was stirred gently, and nitrogen was bubbled through the solution (40 cm$^3$/min).

140 g methoxy polyethyleneglycol 2000 methacrylate (MPEG2000MA) (Inspec) was placed in a 1 liter beaker and dissolved with stirring in 100 ml de-ionised water. Then 36 g methoxy polyethyleneglycol 350 methacrylate (MPEG350MA) (Inspec) was poured into the MPEG2000MA solution. Then 85 g of butyl methacrylate (Aldrich) was poured into the above solution with vigorous stirring.

When the temperature in the 2 liter, 3-necked reaction vessel reached 75° C. the above monomer mixture was poured into the reaction vessel and was stirred vigorously.

20 g of polyhexanide methacrylate was dissolved in 100 ml de-ionised water and was poured into the above reaction vessel containing the monomer mixture. When the temperature inside the reaction vessel reached 80° C., 1 g potassium persulphate (dissolved in 60 ml of de-ionised water) was added to the reaction vessel.

After approximately 10 mins a white viscous emulsion polymer had formed. The polymer was cooled down to room temperature in a water bath and then poured into a dialysis membrane (MWCO 3,000-4000) and dialysed against 10 liters of water for 48 hrs. After 24 hrs, the 10 liters of water was replaced with fresh de-ionised water.

The polymer was removed from the dialysis membrane and poured into freeze-drying trays and was then freeze-dried for 72 hrs.

200 g of a dry white powder of the polymer resulted.

2 g of the above polymer was dissolved in 30 ml isopropanol and when fully dissolved to a clear solution, 70 ml of tetrahydrofuran was added. Polyvinylchloride (PVC) and polyurethane (PU) tubing were coated with this polymer by dipping the tubing into the above polymer solution and then allowing it to dry for 2 hrs. When wetted with water, both the PVC and PU tubings were completely wetted out and were highly lubricious. 10 PVC and 10 PU (length 5 cm) tubings were then incubated at 37° C. in de-ionised water (100 ml) for 72 hrs. They were then removed, washed and tested for wetting. Again both sets of tubings were completely wetted out and there was no diminishing in the lubricity. The de-ionised water in which the PVC and PU tubes were incubated was freeze-dried and re-constituted in 3 ml de-ionised water and the absorbance of the solution was measured at 250 nm. No absorbtion was detected due to the polyhexanide. A 0.0025% w/v solution of polyhexanide, which was used as the control, had an absorption of 0.35 o.d.

Example 9

Polyhexanide Methacrylate Contact Lenses 20 g Ph.P free-base (from Example 6) was dissolved in 300 ml dimethyl sulphoxide. To this was added 1.623 g glycidylmethacrylate (Aldrich) followed by 0.2 g triethylamine. The solution was allowed to stir at 60° C. for 3 hrs. The solution was then neutralised using 0.2M HCl until pH 6.0.

The solution was diluted with water (2 liters) in a dialysis membrane (MW CO: 2,000) against 30 liters of de-ionised water for 24 hrs to remove unreacted glycidylmethacrylate and triethylamine. The solution from the dialysis membrane was then freeze-dried. Yield was 21 g.

Contact lenses were made from the above polyhexanide methacrylate as exactly according to Example 7. The contact lenses produced were clear and transparent. The lenses were hydrated in buffered saline and had a water content of 38%.

20 g of the above polyhexanide methacrylate was polymerised exactly as in Example 8. The polymer was coated onto PVC and PU tubings and assessed for leachables. No polyhexanide leached from either set of tubings as assessed by UV absorption.

Example 10

Polyhexanide Methacrylate Contact Lenses and Coatings 20 g Ph.P free-base (from Example 6) was dissolved in 300 ml ethanol and stirred vigorously. To this solution was added, drop-wise, 1.18 g (7.61×10$^{-3}$ moles) 2-isocyanatoethyl methacrylate (IEM) (Polysciences) dissolved in 50 ml ethanol over a period of 1 hr. This resulted in forming a urethane urea bond between the secondary amine of the polyhexanide and the isocyanate of the IEM. Infrared showed the disappearance of the isocyanate peak due to MM. The reaction between IEM and ethanol does not occur. Even after 24 hrs the isocyanate peak still remains when only IEM and ethanol are present. Isocyanate and alcohol reactions require a catalyst and elevated temperatures for the reaction to be of any significance.

The above solution was then neutralised with 0.19 ml of 4M hydrogen chloride in 1,4 dioxane.

As in Example 9, the above polyhexanide methacrylate was used to make contact lenses (Example 7) and also an emulsion polymer (Example 8). The results were similar to those in Example 9. Polyhexanide methacrylate formed good contact lenses and coated the PVC and PU tubings without any leaching.

Example 11

Polyhexanide Methacrylate Contact Lenses and Coatings 30 g of Ph.P free-base (from Example 6) was dissolved in 300 ml ethanol and stirred vigorously. To this solution was added, drop-wise, 1.760 g (0.0114 moles) methacrylic anhydride (Aldrich) dissolved in 50 ml ethanol over a period of 1 hr. The above reaction resulted in the formation of a tertiary amide and the reaction was followed by the infrared spectrum with the disappearance of the peaks at 1790 cm$^{-1}$ due to C=O asymmetric and symmetric stretching vibrations. In the absence of Ph.P free-base no reaction could be observed between the ethanol and methacrylic anhydride for 10 hrs at 22° C. as observed by infrared. This reaction usually occurs in the presence of a catalyst (e.g. dimethylaminopyridine).

The polyhexanide methacrylate solution was neutralised with 0.285 ml of 4M HCl in 1,4 dioxane. The ethanol was rotary evaporated off and the resulting polymer was dissolved in 100 ml de-ionised water and dialysed in a dialysis membrane (MW CO: 2,000) against 10 L of de-ionised water for 24 hrs. The dialysed solution was then freeze-dried to yield a dry polyhexanide methacrylate (yield, 23 g).

As with previous examples, (Examples 7 and 8), contact lenses and emulsion polymers were made and the results were equivalent to those in Examples 7, 8, 9 and 10.

Example 12

Chlorhexidine Methacrylate 1 g (1.9784×10$^{-3}$ moles) chlorhexidine (Aldrich) was dissolved in 100 ml anhydrous dichloromethane and stirred vigorously. 0.207 g (1.9784×10$^{-3}$ moles) methacryoylchloride was dissolved in 50 ml anhydrous dichloromethane and added drop-wise to the chlorhexidine solution over a period of 1 hr. Methacryloylchloride reacted with the secondary amine of the chlorhexidine forming a tertiary amide. The hydrogen chloride liberated formed one hydrochloride on the chlorhexidine. The reaction was followed by infrared and observed the disappearance of the peaks of methacryloylchloride.

Chlorhexidine methacrylate monohydrochloride was formed in the above reaction. In order to obtain the dihydrochloride, 0.495 ml of 4M hydrogen chloride in 1,4 dioxane was added to the reaction mixture.

The solvent was rotary evaporated off to leave a dry powder of chlorhexidine methacrylate dihydrochloride (CMD).

Example 13

Chlorhexidine Methacrylate 1 g (1.9784×10$^{-3}$ moles) chlorhexidine was dissolved in 100 ml anhydrous dichloromethane and stirred vigorously. 0.3067 g (1.9784×10$^{-3}$ moles) 2-isocyanatoethyl methacrylate (IEM) was dissolved in 50 ml anhydrous dichloromethane and added drop-wise to the chlorhexidine solution over a period of 1 hr. IEM reacted with the secondary amine of the chlorhexidine to form a urethane urea bond. Infrared showed the disappearance of the isocyanate peak due to IEM.

The above reaction resulted in the formation of chlorhexidine methacrylate. In order to obtain the dihydrochloride, 0.99 ml of 4M hydrogen chloride in 1,4 dioxane was added to the reaction mixture. The solvent was rotary evaporated to yield chlorhexidine methacrylate dihydrochloride.

Example 14

Chlorhexidine Amide Linkage with Methacrylic Acid 1 g (8.293×10$^{-3}$ moles) trimethylacetyl chloride was dissolved in 50 ml anhydrous dichloromethane. To this was solution added 0.839 g distilled triethylamine and the solution stirred. 0.714 g (8.293×10$^{-3}$ moles) methacrylic acid was dissolved in 25 ml anhydrous dichloromethane and added drop-wise to the above mixture and stirred for 3 hrs at 22° C. This reaction resulted in the formation of a mixed anhydride.

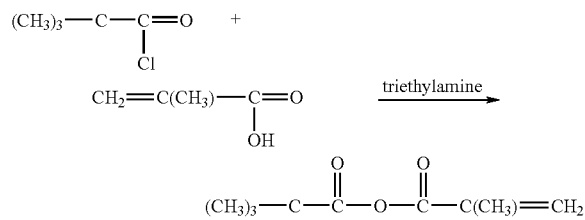

The dichloromethane was rotary evaporated leaving a liquid mixed anhydride.

1 g (1.9784×10$^{-3}$ moles) chlorhexidine was dissolved in 100 ml anhydrous dichloromethane and stirred vigorously.

The above mixed anhydride was then reacted on a mole to mole basis with the chlorhexidine. The number of grams of mixed anhydride required was 0.3363 g (1.978×10$^{-3}$ moles). However, to allow for the triethylamine hydrochloride in the mixture, the number of grams required is 0.61 g. Accordingly 0.61 g of the mixed anhydride mixture was dissolved in 50 ml anhydrous dichloromethane and added dropwise to the chlorhexidine solution over a period of 1 hr. The methacrylic acid formed a tertiary amide with the secondary amine of the chlorhexidine and the trimethyl acetic acid formed the counter ion to form chlorhexidine methacrylate mono trimethylacetate. 0.495 ml of 4M hydrogen chloride in 1,4 dioxane was added to form the other counter ion. The solution was rotary evaporated to dryness and a dry powder of the product obtained.

Chlorhexidine will preferentially react with the methacrylic acid of the mixed anhydride and not the trimethylacetic acid because the latter is sterically hindered.

Example 15

Chlorhexidine Methacrylate Homopolymer 10 g (0.01978 moles) chlorhexidine was dissolved in 60 ml anhydrous dimethylsulphoxide under nitrogen at 40° C. (approximately 30 mins) in a 3-necked round bottom flask with overhead stirring. The solution was allowed to cool to room temperature and then 2.81 g glycidyl methacrylate was added, followed by 0.2 g triethylamine. The solution was allowed to react for 4 hrs at 60° C. with stirring. Then the dihydrochloride salt was formed by adding 10 ml of 4M hydrogen chloride in 1,4 dioxane to give chlorhexidine methacrylate dihydrochloride.

Nitrogen was then bubbled through the solution and the temperature of the solution allowed to reach 75° C. when 0.1 g 2,2'-azobis (2,4-dimethylvaleronitrile) was added as initiator. The solution became highly viscous after 15 min polymerisation at 80° C. and at 30 min the reaction was stopped by cooling the solution. The homopolymer of chlorhexidine was precipitated by adding 500 ml de-ionised water. The polymer was washed several times with water before drying in a vacuum oven at 60° C. for 24 hrs.

Example 16

Chlorhexidine Methacrylate

Chlorhexidine methacrylate dihydrochloride was made exactly as according to Example 15 except that the solvent used was anhydrous chloroform. The chloroform was rotary evaporated to leave a dry white powder.

Example 17

Contact Lens Material Containing Chlorhexidine Methacrylate Polymer 20 mg chlorhexidine methacrylate (from Example 12) was dissolved in 10 ml 2-hydroxyethyl methacrylate with gentle warming (30° C.). Then 40 mg ethylene glycol dimethacrylate and 20 mg 2,2'-azobis (2,4-dimethylvaleronitrile) was added to the solution and stirred until a clear solution was obtained. The solution was then de-gassed for 30 mins.

The above polymerisation mixture was poured into a polypropylene concave mould and then a polypropylene convex mould was placed onto the concave mould allowing the excess solution to overflow thereby uniformly filling the space between the concave and convex moulds. The shape of the concave and convex moulds approximates a contact lens. The sealed moulds were then heated to a temperature of 65° C. for 4 hrs and then at 110° C. for 1 hr to cure the lens.

The moulds were then cooled, opened and contact lenses were obtained. The lenses produced were clear and transparent. The lenses were hydrated in phosphate buffered saline for 6 hrs. The water content was measured and found to be 38%.

Contact lens material was also made in a similar manner from the chlorhexidine methacrylate synthesised in Examples 13, 14 and 16 and they all produced good clear contact lenses with water content being 38%.

Example 18

Chlorhexidine/Polyisophorone Urethane Polymer 3 g (5.935×10$^{-3}$ moles) chlorhexidine was dissolved in 100 ml anhydrous dichloromethane with stirring. 4 g (2.963×10$^{-3}$ moles) PNGAID was dissolved in 50 ml anhydrous dichloromethane and added drop-wise to the chlorhexidine solution over a period of 1 hr. When the reaction was complete, infrared showed the absence of the bond at 2265.9 cm$^{-1}$ due to N=C=O group of PNGAID. The reaction resulted in forming a urethane urea bond. 2 mole equivalent of chlorhexidine reacted with one mole equivalent of PNGAID.

Then the dihydrochloride was formed by adding 2.97 ml of 4M hydrogen chloride in 1,4 dioxane. Five 5 cm long PU tubings were dip-coated with this polymer and allowed to dry for 24 hrs. The PU tubing was then placed in de-ionised water (100 ml) at 37° C. for 72 hrs, after which the tubes were removed and the de-ionised water was freeze-dried. 3 ml of anhydrous dichloromethane was used to wash the stainless steel tray in which the de-ionised water was freeze-dried. A potassium bromide crystal was coated with the washing of dichloromethane and then infrared spectroscopy was conducted. Infrared showed no peak which related to the chlorhexidine or to the PNGAID.

Example 19

Fungistatic and Bacteriostatic Activity

The silicone sheets produced in Example 5 were exposed to the following yeast, fungi and bacteria: *Candida albicas, Aspergeillus niger, Staphylococcus epidermis, Escherichia coli, Staphylococcus aureus* and *Bacillus subtilis.*

The sheets were incubated for 12 days at 30° C. The microorganism growth is tabulated below.

| Organism Polyhexanide | Control Silicone Sheet Growth per $cm^2$ ($\times 10^6$) | Silicone incorporating Growth per $cm^2$ ($\times 10^6$) |
| --- | --- | --- |
| *Candida albicas* | 60.8 | 2.1 |
| *Aspergeillus niger* | 75.3 | 2.8 |
| *Staphylococcus epidermis* | 53.8 | 0.3 |
| *Escherichia coli* | 83.7 | 0.4 |
| *Staphylococcus aureus* | 40.6 | 0.2 |
| *Bacillus subtilis* | 68.9 | 0.2 |

Example 20

Fungistatic and Bacteriostatic Activity

Coated polyurethane (PU) tubing pieces (3 cm long) from Example 8 (polyhexanide coated) and from Example 18 (chlorhexidine coated) were exposed to the same micro-organisms as in Example 19 and the results are tabulated below.

| Organism | Uncoated (PU) Growth per $cm^2$ ($\times 10^6$) | PU coated (polyhexanide) Growth per $cm^2$ ($\times 10^6$) | PU coated (chlorhexidine) Growth per $cm^2$ ($\times 10^6$) |
| --- | --- | --- | --- |
| *Candida albicas* | 83.2 | 2.1 | 7.4 |
| *Aspergeillus niger* | 50.6 | 1.1 | 6.5 |
| *Staphylococcus epidermis* | 110.0 | 2.8 | 7.3 |
| *Escherichia coil* | 90.0 | 1.1 | 4.6 |
| *Staphylococcus aureus* | 30.0 | 0.2 | 2.0 |
| *Bacillus subtilis* | 45.2 | 0.1 | 4.0 |

The invention claimed is:

1. A polymeric material comprising an infection resistant biguanide-containing moiety pendant to a polymer chain, wherein the biguanide-containing moiety comprises a plurality of biguanide groups and is chemically bound to the polymer chain though some but not all of the secondary amine nitrogen atoms of a biguanide group, wherein said chemical binding is via a substituted urea linkage or a substituted thiourea linkage or a N,N-disubstituted amide linkage or a N,N-disubstituted hemiaminal or aminal linkage or a tertiary amine linkage.

2. A polymeric material according to claim 1 wherein the infection resistant biguanide-containing moiety is chlorhexidine or polyhexanide.

3. A medical device comprising a polymeric material incorporating an infection resistant biguanide-containing moiety pendant to a polymer chain, wherein the biguanide-containing moiety comprises a plurality of biguanide groups and is chemically bound to the polymer chain though some but not all of the secondary amine nitrogen atoms of a biguanide group, wherein said chemical binding is via a substituted urea linkage or a substituted thiourea linkage or a N,N-disubstituted amide linkage or a N,N-disubstituted hemiaminal or aminal linkage or a tertiary amine linkage.

4. A medical device according to claim 3 wherein medical device is first formed from or coated with polymeric material which is thereafter reacted with an infection resistant biguanide-containing moiety such that the biguanide-containing moiety is chemically bound to the polymer chain though some but not all of the secondary amine nitrogen atoms of a biguanide group, wherein said chemical binding is via a substituted urea linkage or a substituted thiourea linkage or a N,N-disubstituted amide linkage or a N,N-disubstituted hemiaminal or aminal linkage or a tertiary amine linkage.

5. A medical device according to claim 3 formed as a contact lens or intra-ocular lens.

6. A polymeric material incorporating a polyhexanide moiety pendant to a polymer chain, wherein the polyhexanide moiety is chemically bound to the polymer chain though some but not all of the secondary amine nitrogen atoms of a biguanide group of the polyhexanide moiety, and the chemical binding is via N,N-disubstituted amide linkage.

7. A medical device according to claim 3 wherein medical device is first formed from or coated with polymeric material which is thereafter reacted with an infection resistant biguanide-containing moiety comprising a plurality of biguanide groups such that the biguanide-containing moiety is chemically bound to the polymer chain though some but not all of the secondary amine nitrogen atoms of a biguanide group of the infection resistant biguanide-containing moiety, and the chemical binding is via a substituted urea linkage, or a substituted thiourea linkage, or a N,N-disubstituted amide linkage or a N,N-disubstituted hemiaminal or aminal linkage or a tertiary amine linkage.

* * * * *